United States Patent [19]

Wilson

[11] Patent Number: 5,443,527
[45] Date of Patent: Aug. 22, 1995

[54] PROSTHETIC FOOD AND THREE-WAY ANKLE JOINT

[76] Inventor: Michael T. Wilson, 3131 Villa La., Missouri City, Tex. 77459

[21] Appl. No.: 40,905

[22] Filed: Mar. 31, 1993

[51] Int. Cl.⁶ ............................. A61F 2/66; A61F 2/62
[52] U.S. Cl. ......................................... 623/49; 623/52; 623/53; 623/38; 403/120; 403/132
[58] Field of Search ............... 623/52, 50, 49, 48, 623/38, 53, 55; 403/120, 132

[56] References Cited

U.S. PATENT DOCUMENTS

| | | | |
|---|---|---|---|
| 409,311 | 8/1889 | Snyder | 623/53 X |
| 419,019 | 1/1890 | Kolbe | 623/54 X |
| 1,071,230 | 8/1913 | Hanger | 623/54 X |
| 1,294,632 | 2/1919 | Dickson . | |
| 2,450,728 | 10/1948 | Havens | 623/52 X |
| 2,594,752 | 4/1952 | Fahlst0m | 403/120 X |
| 2,731,645 | 1/1956 | Woodall | 623/53 X |
| 3,196,463 | 7/1965 | Farneth | 623/49 |
| 3,480,972 | 12/1969 | Prahl | 623/50 |
| 3,945,737 | 3/1976 | Herbenar | 403/132 X |
| 3,982,278 | 9/1976 | May | 623/38 |
| 4,328,594 | 5/1982 | Campbell et al. . | |
| 4,446,580 | 5/1984 | Furuya et al. | 623/53 |
| 4,461,045 | 7/1984 | Shorter et al. . | |
| 4,463,459 | 8/1984 | Shorter et al. . | |
| 4,547,913 | 10/1985 | Phillips | 623/27 |
| 4,645,509 | 2/1987 | Poggi et al. | 623/55 |
| 4,721,510 | 1/1988 | Cooper et al. | 623/55 |
| 4,764,172 | 8/1988 | McCoy | 623/49 |
| 4,822,363 | 4/1989 | Phillips | 623/27 |
| 4,889,458 | 12/1989 | Taylor | 411/383 |
| 4,892,554 | 1/1990 | Robinson | 623/55 |
| 4,969,911 | 11/1990 | Greene | 623/38 |
| 5,030,239 | 7/1991 | Copes | 623/52 |
| 5,258,038 | 11/1993 | Robinson et al. | 623/49 |

FOREIGN PATENT DOCUMENTS

| | | | |
|---|---|---|---|
| 1233031 | 10/1969 | France | 623/50 |
| 92017135 | 10/1992 | WIPO | 623/48 |

OTHER PUBLICATIONS

Flex-Foot, Inc. flyers entitled, "Something Revolutionary Is In The Air," Adjust the foot, not the lifestyle, Engineered For The Long Run, Simply Precise, Engineered Flexibility, Designed For A Growing Market, Amputee Profile (Mary Jane Gardner), Amputee Profile (Dan Broome), and Flex-Foot, Inc. Newsletter, Issue No. 4, 1992.
Otto Bock flyer, "1M1-Otto Bock Multiaxial Foot".
Campbell-Childs, Inc. brochure and flyer entitled, "The All New 'Sportsman' S.A.F.E. II".
Devcon instruction sheet on "Flexane ® Urethane".
Boston Gear catalogue, Self-Aligning Bearings, p. D68.
Hosmer, The Quantum Foot–Brochure.
Campbell-Childs, Inc. Stationary Attachment Flexible Endoskeleton II Mailer, Jul. 1989.
Campbell-Childs, Inc.-S.A.F.E. Prosthetic Foot Catalog.
United States Manufacturing Company-Multiplex Brochure.
The Ohio Willow Wood Co., Step into the Future with the Carbon Copy II Energy Storing Foot.
Footnotes (Flex-Foot)-Mailer, Mar. 1989.
Flex-Foot, Inc.-Price List.

*Primary Examiner*—David H. Willse
*Attorney, Agent, or Firm*—Marcella D. Watkins

[57] ABSTRACT

A lightweight foot prosthesis is claimed, having a heel, a toe, and a raised instep, the instep including an upper surface and a lower surface, an ankle joint connected to the foot and capable of motion around each of three perpendicular axes, a pair of compression mounts for limiting rotation of the ankle joint, and a connector for connecting the ankle joint to a leg.

11 Claims, 9 Drawing Sheets

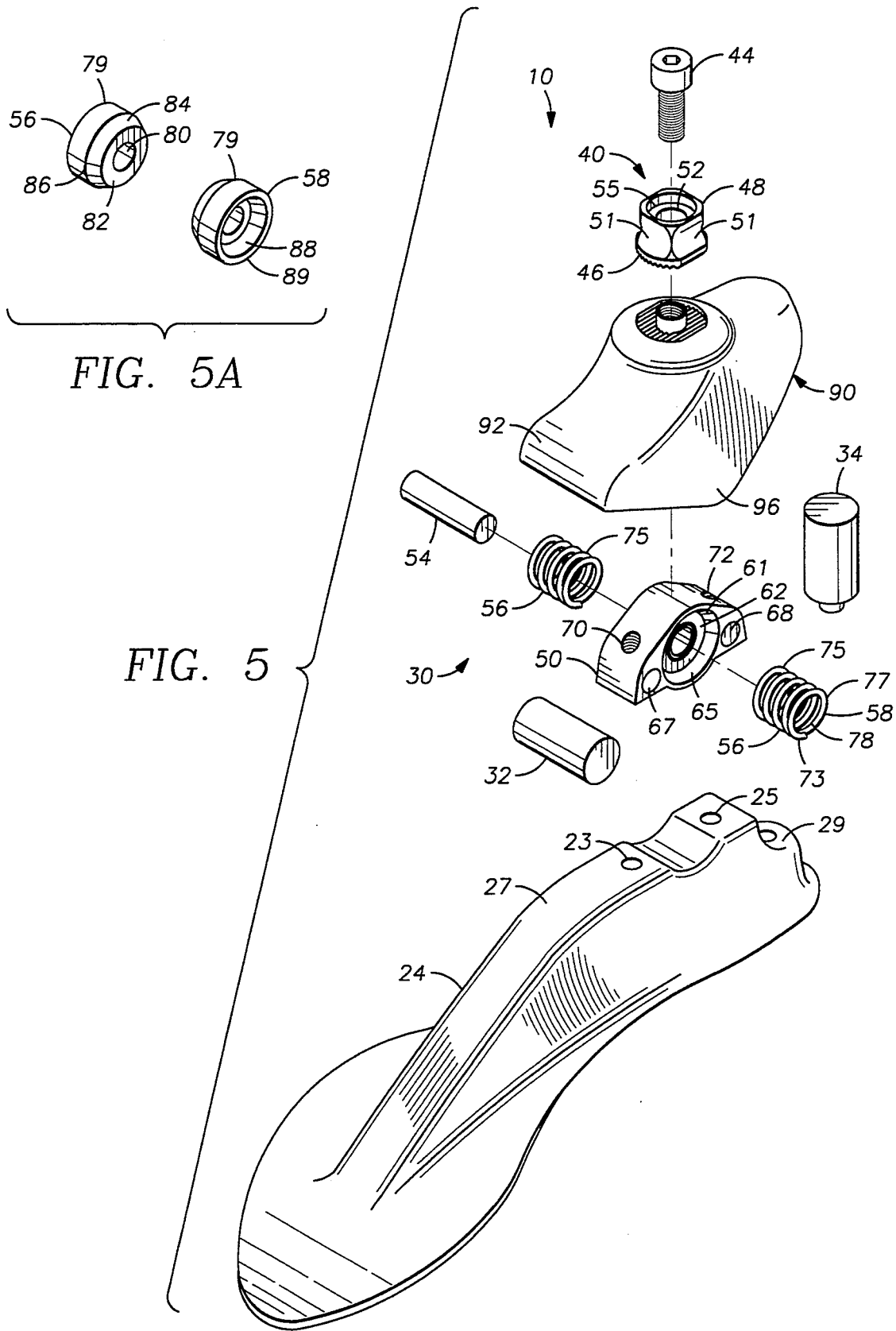

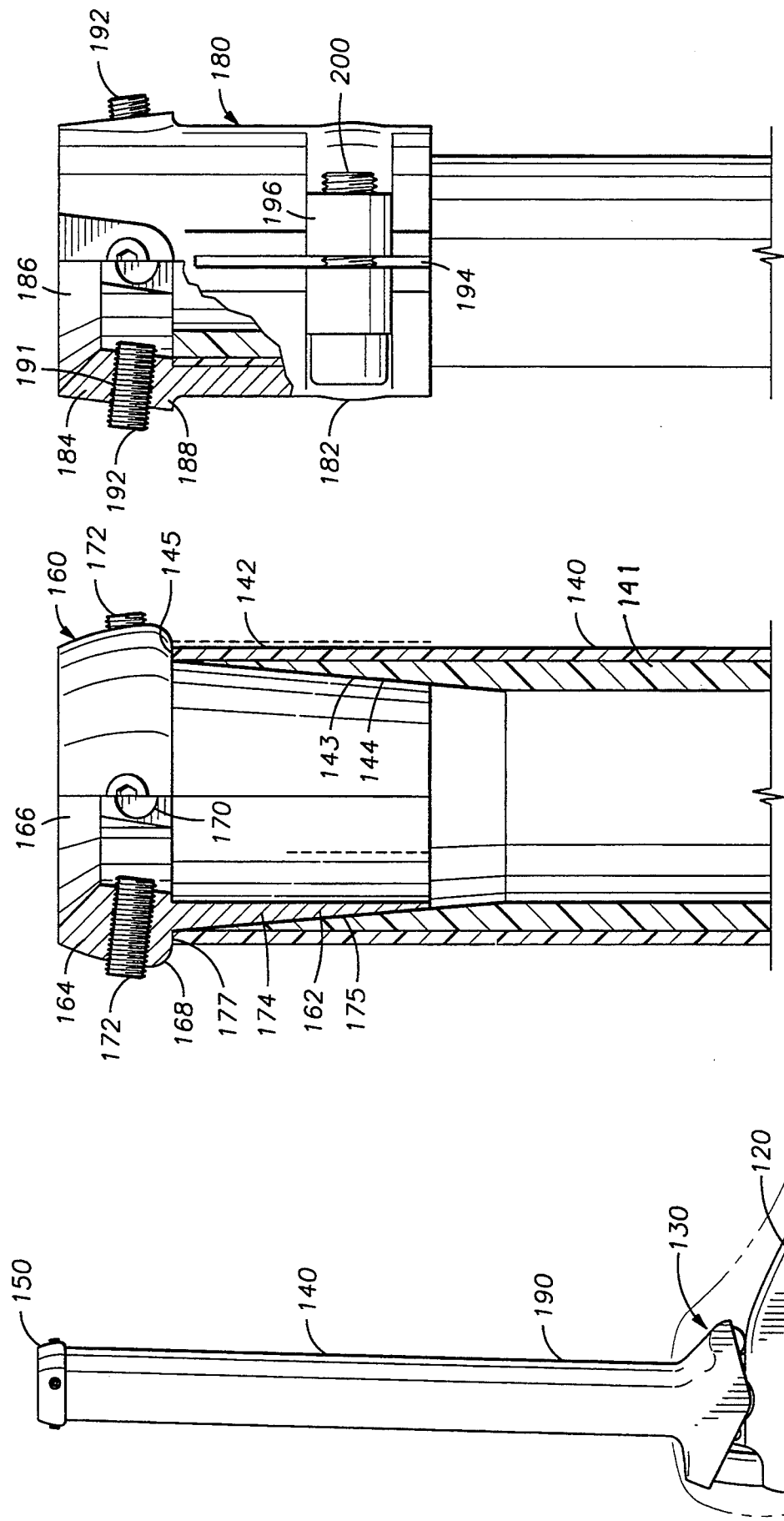

PROSTHETIC FOOD AND THREE-WAY ANKLE JOINT

TECHNICAL FIELD OF THE INVENTION

The present invention relates to the foot section of an artificial leg and more particularly to a prosthetic foot specifically designed for geriatric users and others who require less massive prostheses. Still more particularly, the present invention relates to construction of a prosthetic foot and ankle joint adapted to provide a desired degree of mobility without excessive bulk.

BACKGROUND OF THE INVENTION

Prosthetic feet are well known in the art, and several such feet have been designed to accomplish one or more objectives.

A useful prosthesis must simulate the operation and motion of an anatomical foot. An anatomical foot, including the ankle joint, is capable of motion around three perpendicular axes, as well as varying degrees of flexure. Specifically, the anatomical foot and ankle are capable of dorsiflexion, planiflexion, inversion, eversion, and transverse rotation. Dorsiflexion and planiflexion comprise the movement up and down of the ball of the foot with respect to the heel that occurs during a normal forward step. Inversion and eversion are the twisting of the foot around its longitudinal axis, resulting in outward and inward tilting of the ankles, respectively. Transverse rotation occurs when the foot rotates with respect to the longitudinal axis of the leg, such as occurs during left and right turns of the body.

Known foot prostheses include commercial feet that are capable of all three types of rotation. Typically, however, the joints capable of such complicated motion require bulky moving parts and are generally far too heavy for geriatric or very young patients, or other patients who suffer some degree of muscular weakness.

In addition, it is desirable for a foot prosthesis to be capable of absorbing, storing, and releasing energy, so that the prosthesis returns itself to a relaxed, unflexed position when the moving force is removed. Prostheses that are designed for use during athletic activities, such as running or playing basketball, are particularly efficient at energy storage and return, providing a springy step. Such energy storage is typically accomplished by the inclusion of coil springs or other reciprocating means which absorb energy on flexure and release it efficiently upon removal of the applied force. The energy-storing components that are typically used for efficient return can contribute significantly to the weight of the prosthesis.

In contrast, older, less mobile wearers neither need nor want a high degree of return of stored energy. Instead, it is preferable for the prostheses worn by these wearers to absorb and dissipate a portion of the energy of each flexion. This provides a more stable, cushioned step, and reduces the shock experienced by both the wearer and the prosthesis at each step.

Finally, it is necessary that a foot prosthesis be strong enough to support its wearer and durable enough to withstand the stresses of repeated stepping motions over long periods of time. Conventional prostheses tend to be designed for maximized strength, at the cost of added bulk and weight, making them unsuitable for geriatric or very young wearers, who do not subject their prostheses to the same loads as the average wearer.

Hence it is desired to provide a flexible, durable prosthesis that provides a slightly damped step and requires a minimal mass.

SUMMARY OF THE INVENTION

The present invention comprises a foot prosthesis having a light-weight foot portion and an attached light-weight ankle portion capable of a desired degree of rotation around each of three perpendicular axes. As used herein, the words "prosthesis" or "foot prosthesis" will refer to both the foot portion of a prosthetic foot and the ankle joint attached thereto.

Simplified construction of the foot and joint mechanism enables the present invention to be at least about 50% lighter than typical foot prostheses. The foot portion includes an integral instep and sole constructed of light weight polymeric material and is designed to provide support and flexure without added weight. The ankle portion includes a single swivel joint that provides the desired flexibility and stability without excessive mass. Other objects and advantages of the present invention will appear from the following description.

BRIEF DESCRIPTION OF THE DRAWINGS

For a detailed description of a preferred embodiment of the invention, reference will now be made to the accompanying drawings wherein:

FIG. 5 is an exploded view of the prosthetic foot of FIG. 1 without the cosmesis;

FIG. 5A is a perspective view of an alternate embodiment of two components shown in FIG. 5;

FIG. 13 is a side elevational view of a second embodiment;

FIG. 14 is a partially cut away elevation of a connector affixed to the top of the embodiment of FIG. 13; and FIG. 15 is a partially cut away elevation of an alternative connector affixed to the top of the embodiment of FIG. 13.

DETAILED DESCRIPTION OF THE INVENTION

The present invention comprises a lightweight foot prosthesis, an ankle joint affixed to said foot, said foot capable of motion around each of three perpendicular axes, means for limiting rotation of said ankle joint and means for connecting said ankle joint to a leg. The foot portion includes a foot having a dorsal surface and a plantar surface and comprising a heel, a toe and a raised instep.

Referring initially to FIGS. 1-4, the prosthetic foot 10 of the present invention includes a foot 20, an attached ankle joint 30, and a connector 40. A prosthetic shin, or leg, which would normally be attached to connector 40 via a conventional connection is shown in phantom. For purposes of discussion, the x, y, and z axes, about which the foot is designed to rotate, are shown and have been assigned as follows. The x axis is perpendicular to both the leg and foot, passing through the sides of the ankle. The y axis is perpendicular to the leg and parallel to the foot, and the z axis is parallel to the leg.

Figure 1:
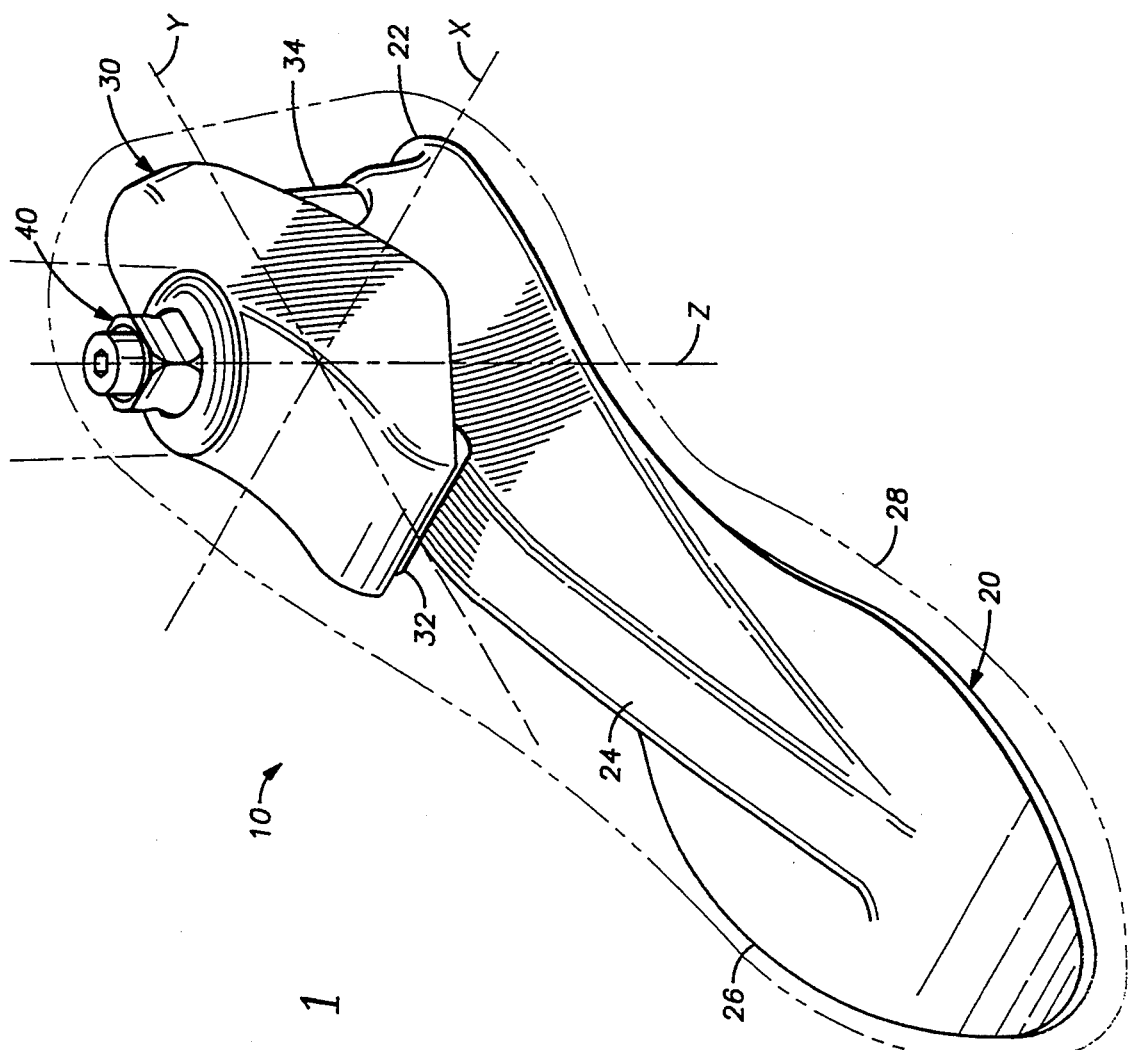
FIG. 1 is a perspective view of the prosthetic foot of the present invention wherein the surrounding cosmesis is shown in phantom.

Still referring to FIGS. 1-4, foot 20 comprises a heel 22, a raised instep 24, and a substantially flat toe portion 26. Together, the heel, instep and toe 22, 24, 26 form a foot that closely replicates the structure and form of an anatomical foot. FIG. 1 also shows in phantom a cosmesis 28, which is molded around prosthetic foot 10. Cosmesis 28 is preferably constructed of foamed polyethylene.

It is preferred that the x axis, which passes through joint 30, be approximately twenty-five percent (25%) of the distance from heel 22 to toe 26. In addition, it is preferred that the transition from instep 24 to toe 26 occur at approximately seventy-five percent (75%) of the distance from heel 22 to toe 26.

Foot portion 20 is preferably constructed of a molded copolymer comprising approximately 90% polypropylene and approximately 10% polyethylene. It has been found that this copolymer combines heat formability with a desired degree of strength and impact resistance. Other materials having these desired physical properties may be substituted for these polymers without departing from the spirit of the invention. Foot portion 20 is formed by molding a working piece of the copolymer around a rigid model having a desired shape. It has been found advantageous to at least partially evacuate a region adjacent to the model. This allows the surrounding atmosphere outside the working piece to apply isostatic pressure to the piece, thereby causing it to conform smoothly and completely to the form. Alternatively foot portion 20 may be injection molded. For lightness, the molded underside (not shown) of raised instep 24 may include a hollow recess, as discussed in greater detail below.

A forward snubber 32 and a rear snubber 34 are interposed between foot portion 20 and ankle joint 30 as discussed in greater detail below. Snubbers 32 and 34 comprise cylindrical resilient members and are preferably constructed of rubber, neoprene, high density urethane, or the like. A preferred material for the construction of snubbers 32, 34 is a polyurethane sold under the registered trademark Flexane ® and manufactured by ITW Devcon, 30 Endicott St., Danvers, Mass. 01923.

Figure 4:
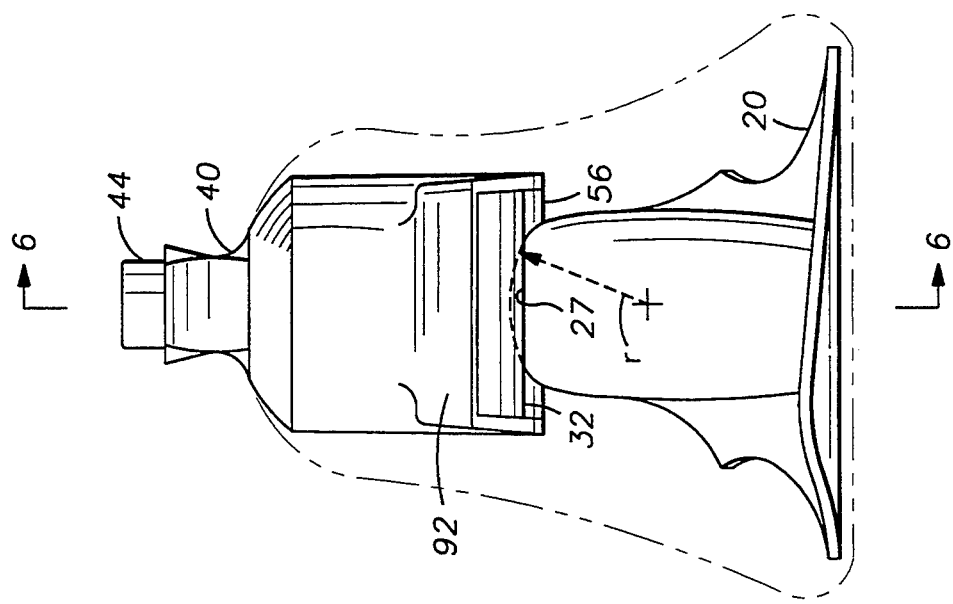
FIG. 4 is a front elevational view of the prosthetic foot of FIG. 1.
Figure 3:
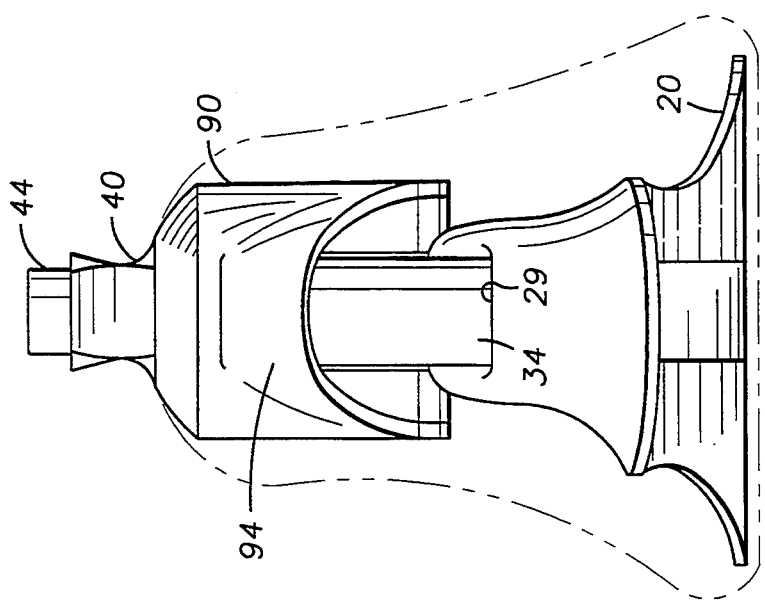
FIG. 3 is a rear elevational view of the prosthetic foot of FIG. 1.

Referring now to FIG. 5, the components of prosthesis 10 are shown in exploded form. Instep 24 includes a forward bore 23 and a rear bore 25 therethrough. Instep 24 includes a curved front contact surface 27 and a planar rear contact surface 29 on its upper, or dorsal surface. As best shown in FIG. 4, contact surface 27 has a radius of curvature r. Ankle joint 30 comprises a body 50, a shaft 54, a pair of compression mounts 56, 58, and a shell 90. Shell 90 includes a forward cup 92, a rear cup 94 and a pair of side portions 96. Shell 90 houses body 50, shaft 54 and compression mounts 56, 58 as described in detail below.

Figure 6:
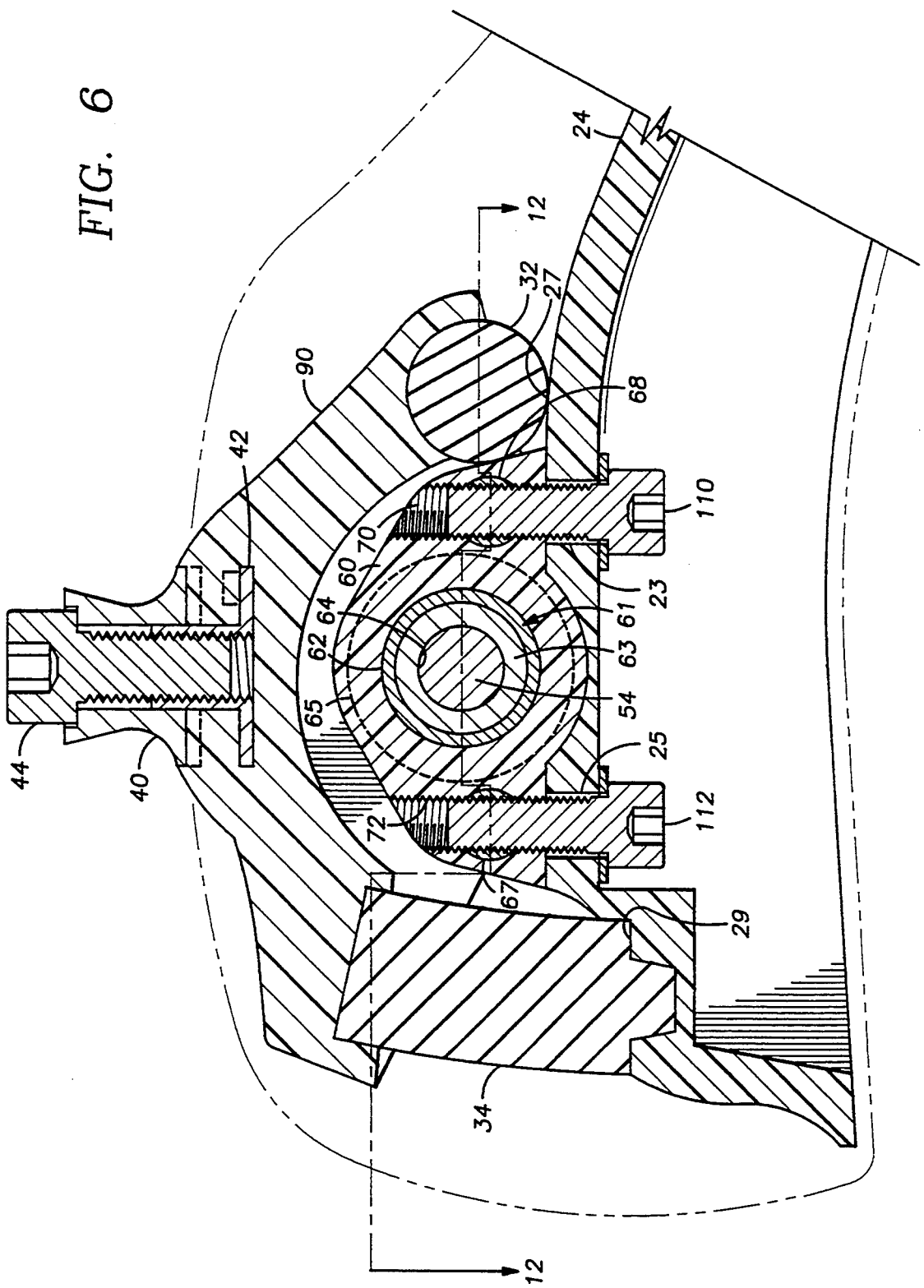
FIG. 6 is a cross-sectional view taken along lines 6—6 of FIG. 4.
Figure 7:
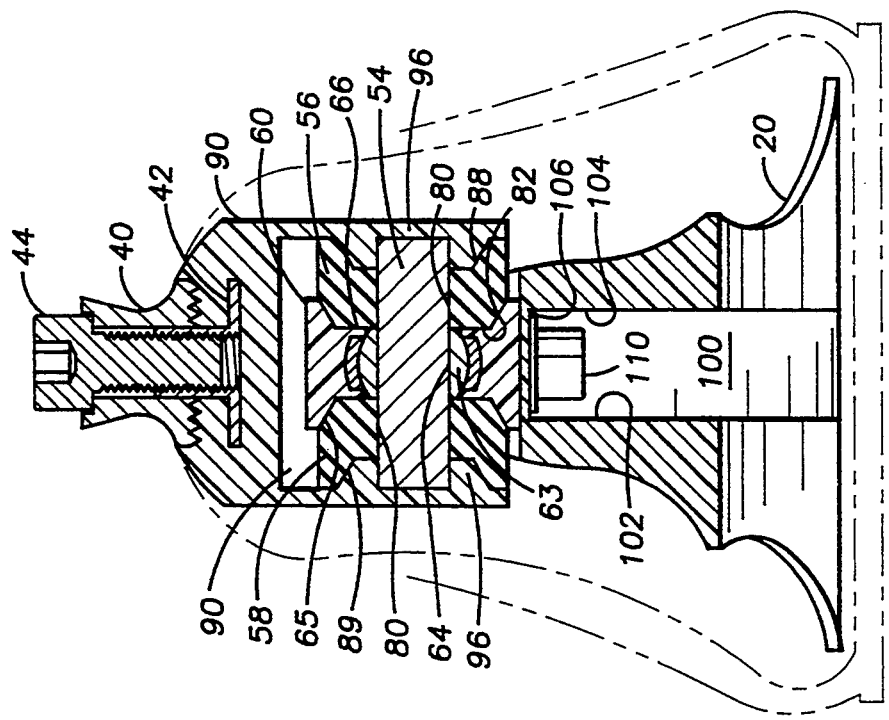
FIG. 7 is a cross-sectional view taken along lines 7—7 of FIG. 2.

As best shown in FIGS. 6-7, body 50 includes an oblong housing 60 in which a swivel joint 61 is transversely mounted. Swivel joint 61 includes an outer race 62 (shown in phantom). Outer race 62 supports an inner race 63. Inner race 63 is rotatable within outer race 62 and has a central bore 64 therethrough. Bore 64 is adapted to receive shaft 54, such that shaft 54 lies on the x axis. Such swivel joints are commonly available, one being manufactured by Boston Gear, a subsidiary of Incom International, Inc. of Quincy, Mass.

Shaft 54 must be capable of withstanding significant shear stresses. Therefore, it is preferable that shaft 54 be constructed of hardened steel. Specifically, commercially available roll pins have been found suitable for use as shaft 54.

Still referring to FIGS. 6 and 7, each side face of housing 60 includes an annular bevel 65 centered on swivel joint 61. Bevel 65 forms an annular seating face 66. Parallel to and proximate swivel joint 61 are a forward transverse support 67 and a rear transverse support 68. A pair of vertical bores 70, 72 pass through body 50, intersecting transverse supports 67 and 68, respectively. For structural purposes, it is desired that the diameter of supports 67, 68 exceed the diameter of bores 70, 72. This ensures that a portion of each support extends beyond the bore, as shown.

According to the preferred embodiment, housing 60 is formed by winding unidirectional glass fiber circumferentially around the outer race 62 of swivel joint 61, and continuing the winding around and adjacently positioned transverse supports 67, 68 to form the oblong housing shape. The glass fiber is then impregnated with an epoxy, to form a rigid, durable body.

Referring again to FIG. 5, compression mounts 56 and 58 preferably comprise identical cylindrical coil springs 75, each having an inner end 76, an outer end 77 and a coaxial opening 78. Inner ends 76 are sized and shaped to receive the ends of shaft 54, and are sized to seat on seating face 66 within bevel 65 of housing 60. In an alternate embodiment, outer ends 77 may have a slightly larger diameter than inner ends 76.

According to a second alternate embodiment, shown in FIG. 5A, each compression mount 56, 58 comprises a solid resilient annulus 79 having a central bore 80 therethrough. Central bore 80 corresponds to opening 78 of the preferred embodiment and is sized to receive shaft 54. The inner face 82 of each annulus 79 is substantially flat and is sized to rest on seating face 66. Adjacent inner face 82 is a bevel 84 which extends to outer circumference 86 and corresponds to bevel 65. The outer face of each annulus 79 comprises a concave face 88 and an adjacent circumferential lip 89. In this second embodiment, annuli 79 are preferably molded of a tough, resilient material, such as rubber, neoprene, high density urethane, or the like. As with snubbers 32, 34, discussed above, a preferred material for the construction of resilient compression mounts 56 , 58 is Flexane ® manufactured by Devcon, see address above.

Still referring to FIG. 5, connector 40 is affixed to shell 90 by means of a T-nut 42 and a bolt 44. Connector 40 comprises an annular flange 46 adjacent one end of a coaxial four-sided body 48. The lower face of flange 46 preferably includes a plurality of longitudinal grooves 49 that run from the front to the back of the flange. Body 48 includes four curved faces 51 and a central bore 52 therethrough. Surrounding bore 52 is a recess 55, which is adapted to receive the head of bolt 44. T-nut 42 comprises an internally threaded body 57 and an adjacent flange 58, which supports four locking tabs 59 (not shown). Preferably, T-nut 42, connector 40 and bolt 44 are made of metal and most preferably of steel.

Connector 40 is the male component of a standard adjustable connection formerly manufactured by the Otto Boch Corp. of West Germany and now widely available. Because of its strength and adjustability, this type of connection is presently used for virtually every non-flexible prosthetic connection.

Referring again to FIG. 7, the relation of shell 90 to connector 40, body 60, shaft 54, compression mounts 56, 58 and foot 20 is shown. When ankle joint 30 is assembled, shaft 54 passes through bore 64 of inner race 63 and through coaxial openings 78 of compression mounts 56, 58. Inner faces 82 rest on seating faces 66 so that the ends of shaft 54 extend through concave faces 88. Shell 90 is constructed so that side portions 96 of shell 90 extend over and encase the ends of shaft 54, forming a permanent connection. In surrounding the ends of shaft 54, the material of side portions 96 is received within the concave faces 88 of compression mounts 56, 58. Between shell 90 and the top of body 60 is a void 98. T-nut 42 is molded into the top of shell 90.

To affix connector 40 to shell 90, connector 40 is seated on T-nut 42 so that the grooves in flange 46 seat in corresponding grooves in shell 90 and prevent connector 40 from shifting laterally with respect to shell 90. Bolt 44 passes through connector 40 and threadingly engages T-nut 42.

Still referring to FIG. 7, instep 24 of foot 20 includes a lower recess 100. Preferably, recess 100 comprises a longitudinal groove in instep 24 having side walls 102, 104 and an inner wall 106. As shown in FIGS. 5 and 4, inner wall 106 includes a pair of bores 23, 25.

According to a preferred embodiment, shell 90 is constructed around connector 40, body 60, shaft 54, compression mounts 56, 58 in a series of steps that result in a strong but relatively light joint. First, shaft 54 is placed through inner race 63 and compression mounts 56, 58 are placed over the ends of shaft 54 and seated against body 60. If springs 75 are used as compression mounts, a conical liner (not shown) is placed within the outer end 77 of each spring, to prevent the flow of epoxy into the spaces between the coils of the spring.

Next, a wax cast is molded around these assembled components. The outer surface of the wax cast is sculpted to correspond to the desired contours of the inner surface of shell 90, including the seats for snubbers 32, 34 in forward and rear cups 92, 94, and the outer contours of void 98. The dorsal surface of the wax cast is then wrapped in fiberglass. Preferably the fiberglass includes the following layers:

| Position | No. of Layers | Weight of Fiber | Type of Glass | Orientation |
| --- | --- | --- | --- | --- |
| 1 | 1 | 6 oz. | bidirectional | front to rear |
| 2 | 1 | 13 oz. | unidirectional | front to rear |
| 3 | 2 | 6 oz. | bidirectional | side to side |
| 4 | 2 | 26 oz. | unidirectional | side to side |
| 5 | 2 | 26 oz. | unidirectional | front to rear* |
| 6 | 1 | 26 oz. | unidirectional | transverse** |

-continued

| Position | No. of Layers | Weight of Fiber | Type of Glass | Orientation |
| --- | --- | --- | --- | --- |
| 7 | N/A | 52 oz. | mat | N/A*** |

*One layer ends in front of T-nut 42 and one passes over T-nut 44.
**This layer extends only across the front end 92 of shell 90.
***Glass mat is shaped to form the dome of joint 30, which serves to restrain T-nut 42 and provide support for a prosthetic leg connection.

Once all of the desired layers of fiberglass have been assembled around the wax cast, the wrapped cast is inserted into a mold, which is then sealed. The mold corresponds to the desired outer surface of shell 90, and includes grooves 99 running from front to back along the uppermost surface. Grooves 99 in shell 90 correspond to the grooves in flange 46 of connector 40. Epoxy is drawn into the void between the cast and the mold, thoroughly impregnating the fibers. Once the shell has been thus formed, the joint is removed from the mold. The wax is melted and removed, leaving the joint shown in FIG. 3 and described above.

By positioning the connection of shell 90 to shaft 55 at least partially within compression mounts 56, 58, the present design allows ankle joint 30 to be narrower along the x axis than it would otherwise be. The narrow shape substantially reduces the weight of the joint and makes it easier for the completed joint to be removed from the mold.

It has been found advantageous to provide ankle joint 30 in a plurality of sizes. Specifically, it has been found that three sizes are adequate to support the normal range of necessary prosthesis sizes. The size of swivel joint 61 varies according to the desired prosthesis size. For example, for a large size prosthesis, central bore 64 of inner race 63 has a diameter of ⅜ inches; a medium prosthesis has a bore of 5/16 inches, and a small prosthesis has a bore of ¼ inch. As mentioned above, shaft 54 is sized to be snugly received within bore 64. Hence, the size of shaft 54 also varies according to the joint size.

It is preferred that the height, or depth, of instep 24 be approximately 10-15 percent of the length of foot portion 20. This allows the cross-section across the y axis of instep 24 to be great enough to provide the necessary rigidity through the middle of the foot, while maintaining the x axis (through bore 64) as low as possible. Another advantage of this relation is that it allows the top and bottom molds for the cosmesis to be approximately equal in volume, making assembly of the prosthesis easier.

Referring now to FIGS. 6 and 7, ankle joint 30 is attached to foot 20 by means of a pair of bolts 110, 112. Bolts 110, 112 pass through bores 23, 25, respectively and engage bores 70, 72, respectively, in body 50. It will be understood that bolts 110, 112 could be replaced with a single bolt, or other suitable attachment means. It is believed advantageous, however, to use at least two such attachment means, as it reduces fatigue in the attachment, even if the attachment(s) develop slack.

When foot 20 is bolted to body 50, snubber 32 is positioned transversely within the forward cup 92 of shell 90 so that it rests on front contact surface 27. Snubber 32 is sized so that its diameter is approximately equal to the distance between contact surface 27 of instep 24 and the underside of forward cup 92 of shell 90. Because contact surface 27 is curved from side to side, only the center portion of forward snubber 32 contacts surface 27 in the normal, unflexed position.

Rear snubber 34 is positioned vertically within the rear cup 94 of shell 90 so that it rests on contact surface 29. Snubber 34 is sized so that its length is approximately equal to the distance between planar surface 29 of instep 24 and the underside of rear cup 94 of shell 90.

Figure 8:
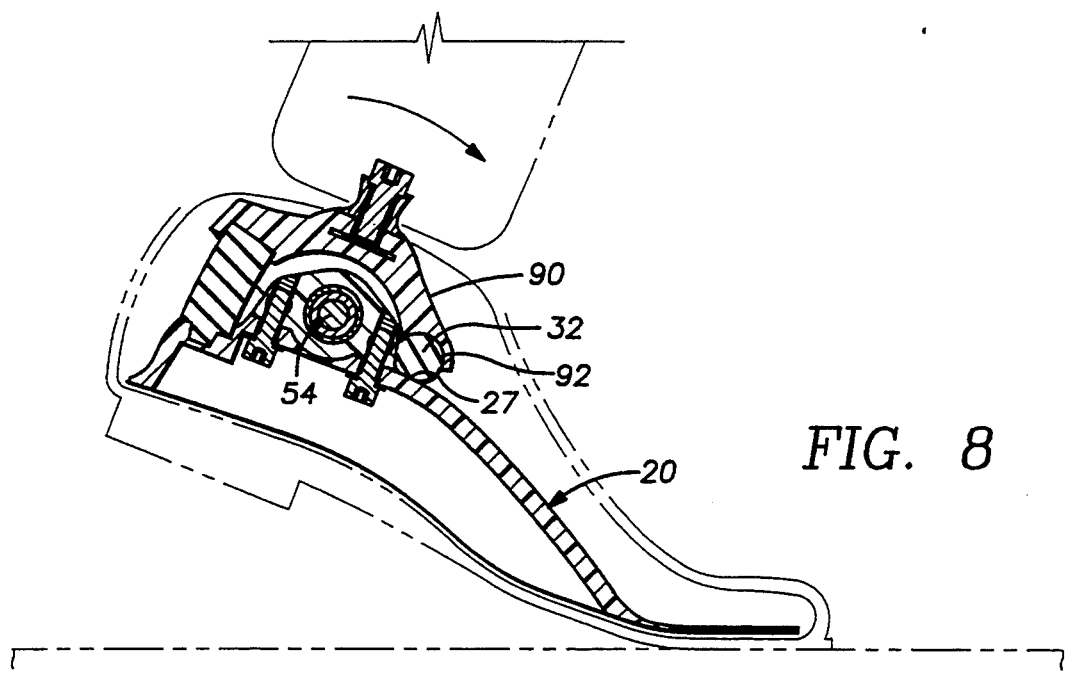
FIGS. 8–10 are sequential side elevational views of the foot of FIG. 1 showing motion of the foot and attached ankle joint through a step.

Referring now to FIG. 8, during dorsiflexion, the leg is inclined toward the front of the foot. Dorsiflexion occurs during the "push-off" phase of a normal step, or during uphill walking. In the prosthesis of the present invention, dorsiflexion causes a clockwise (as shown) moment about the x axis to be applied to shell 90. Because shell 90 is affixed to the ends of shaft 54, shaft 54 rotates within swivel mount 61 as shell 90 pivots. Pivoting of shell 90 causes front snubber 32 to be compressed between front contact surface 27 and forward cup 92. As the degree of flexion increases, snubber 32 deforms to fully contact the curved contact surface 27. Because snubber 32 is resilient and is substantially confined within forward cup 92, it resists compression and biases foot 20 away from forward cup 92. During normal use, a maximum dorsiflexion about shaft 54 of approximately 10 to 15 degrees will occur.

For a given prosthesis size, the degree of dorsiflexion that can occur depends in part on the durometer, or hardness, of forward snubber 32. A desired durometer can be selected by modifying the composition of the snubber material. Methods for altering the durometer of a material, and of polymers in general are well known. If, as discussed above, Flexane ® is used, an additive marketed under the trademark Flex-Add ™ and also manufactured by Devcon, may be used to produce a softer polymer.

The radius of curvature r of contact surface 27 also affects the resistance of joint 30 to dorsiflexion. The smaller the radius of curvature r of contact surface 27, the smaller the area is of surface 27 that contacts snubber 32. With a smaller area, greater pressure will be applied by a given force, causing greater deformation. A surface 27 having a smaller radius of curvature will distort snubber 32 to a greater degree and allow more degrees of dorsiflexion with the same force. Thus, the same effect can be achieved by providing either a softer snubber or a smaller radius of curvature for contact surface 27.

The height of instep 24 can also affect the dorsal flexibility of the prosthetic foot. Because the flexibility of an object depends on its cross-section in the direction of flexure, raising the height of instep 24 produces a stiffer foot. Likewise, a more flexible foot can be produced by decreasing the height of instep 24. Because foot 20 is made substantially of polypropylene in a preferred embodiment, it is capable of some flexure without breaking. As stated above, the height of instep 24 will approximately equal 10–15 percent of the length of foot 20.

Figure 9:
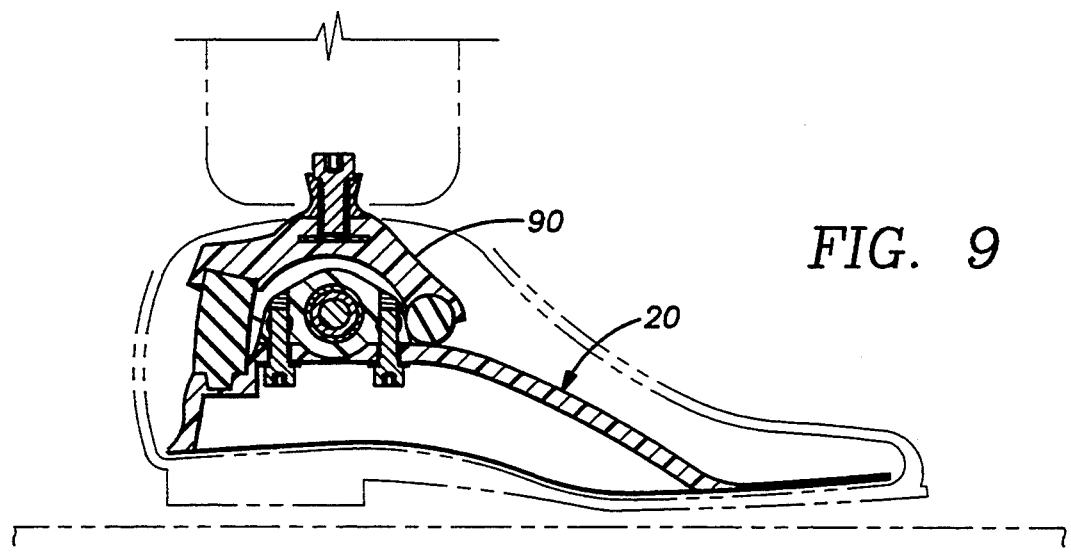

In contrast to instep 24, toe portion 26 of foot 20 has a small cross-sectional area, and therefore flexes relatively easily. Hence, as the wearer's body mass moves forward over the foot and begins to straighten the ankle, the energy stored in front snubber 32 is transferred into flexure of toe portion 26. When the toe of prosthesis 10 leaves the ground, moment is removed from the joint and prosthesis 10 returns to its unflexed position as the leg swings forward, as shown in FIG. 9. It is preferred that joint 30 store only a minimum amount energy, that amount being the amount necessary to return the prosthesis to its unflexed position. It is preferred that excess energy be dissipated within the resilient components of joint 30, so as to avoid an excessively bouncy step. The degree to which energy is dissipated, rather than being released, can be controlled by modifying the composition and structure of the resilient components.

Figure 10:
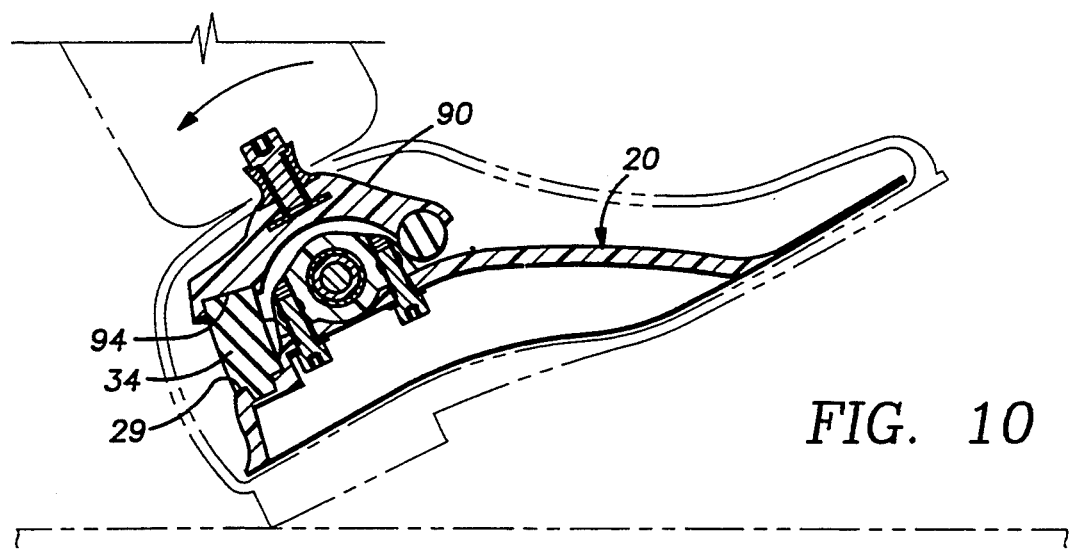

Referring now to FIG. 10, when the heel of prosthesis 10 is placed on the ground, a counter-clockwise moment is applied to the joint, resulting in planiflexion. As in dorsiflexion, shell 90 pivots, this time in a counter-clockwise direction about the x axis, causing shaft 43 to rotate in swivel joint 61. Rear snubber 34 is compressed between rear contact surface 29 of instep 24 and rear cup 94 of shell 90, and biases prosthesis 10 to return to an unflexed position. In addition, rear snubber 34 provides more shock-absorbing capability. Because it is oriented so that the compressive forces are applied along its longitudinal axis, it is capable of compression through a greater distance than the transversely mounted front snubber 32. During normal use, a maximum planiflexion about shaft 54 of approximately 10 to 30 degrees will occur. Once the foot is planted, as the wearer moves forward the moment is removed and prosthesis 10 returns to an unflexed position before commencing the next push-off phase as shown in FIG. 10.

Figure 11:
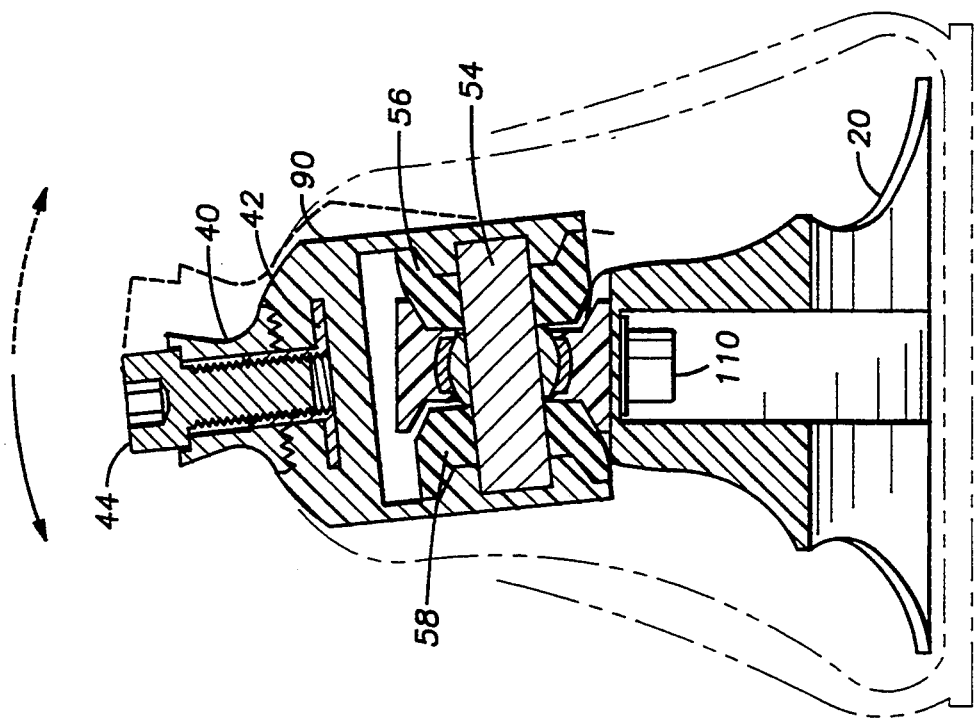
FIG. 11 is a rear elevational view of the prosthetic foot of FIG. 1 showing inversion of the ankle joint, with eversion of the same joint shown in phantom.

Referring now to FIG. 11, the inversion of ankle 30 is shown. In FIG. 11, inversion results in counter-clockwise rotation of shell 90 with respect to foot 20 about the z axis. Eversion is shown in phantom. When ankle 30 inverts or everts while the foot is on the ground, a corresponding moment is applied to shell 90 via connector 40. The moment transmitted via shell 90 tends to force the two ends of shaft 54 in opposite directions. Shaft 54 passing through bore 64 causes inner race 63 to swivel within outer race 62. As shaft 54 swivels, each compression mount 56, 58 is compressed between side portions 96 of shell 90 and housing 60. Because mounts 56, 58 are resilient, they push against bevel 65 and seating face 66, and resist swiveling of shaft 54. Before compression mounts 56, 58 are fully compressed, body 50 reaches its maximum rotation within shell 90 and is prevented by shell 90 from rotating further. During normal use, a maximum rotation of approximately 10 degrees will occur before body 50 contacts shell 90. Because front contact surface 27 is curved, snubber 32 can tilt from side to side with shell 90 without interfering with inversion or eversion of the joint.

The force required to rotate any given joint depends on both the construction and configuration of compression mounts 56, 58. The deeper the conical liners used with springs 75 or the concave faces 88 of annuli 79 are, the more material of side portions 96 of shell 90 will flow into the voids between faces 88 and the ends of shaft 54. Because shell 90 is constructed of a rigid, incompressible material, whereas compression mounts 56, 58 are compressible, decreasing the flexibility of mounts 56, 58 and increasing the amount of shell material surrounding shaft 54 has the effect of limiting the ability of shaft 54 to swivel about the y and z axes. If there is too much space between mounts 56, 58 and the ends of shaft 54, too much material of side portions 96 will enter that space and will excessively reduce the degree of motion of which the joint is capable. Hence, the stiffness of swivel joint 61 with respect to transverse rotation can be controlled through the design of mounts 56, 58.

When prosthesis 10 is removed from the ground, the moment about the z axis is removed and the energy stored in mounts 56, 58 causes foot 20 to re-align itself with shell 90.

Figure 12:
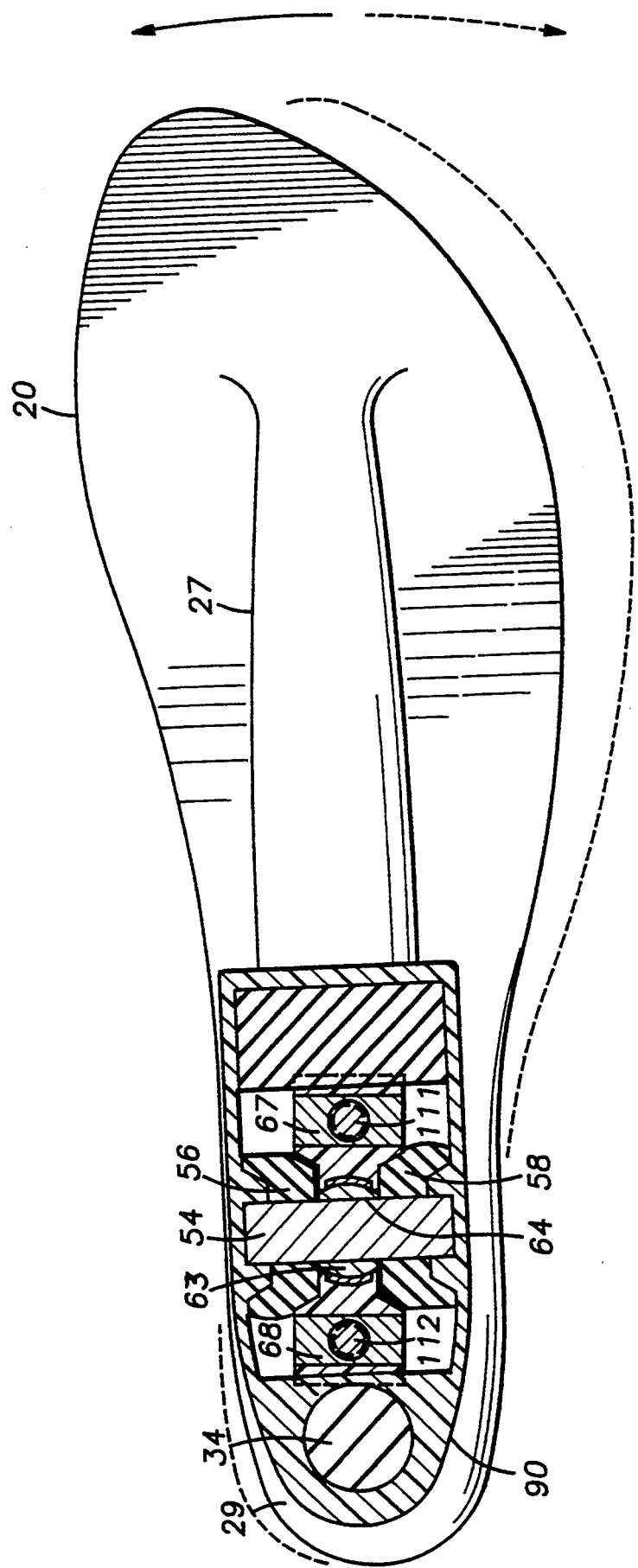
FIG. 12 is a cross-sectional, top view of the foot of FIG. 1 showing left transverse rotation, with right transverse rotation shown in phantom.

Left and right transverse rotation as shown in FIG. 12 are accomplished in the same manner as transverse rotation. That is, rotation of the ankle to either the left or right about the z axis, as shown in FIG. 10, results in a moment applied to shell 90. The moment is transmitted through side portions 96 to the ends of shaft 54. Shaft 54 causes inner race 63 to swivel within outer race 62. Compression mounts 56, 58 are again compressed between the ends of shaft 54 and bevel 65. The energy stored in compression mounts 56, 58 can be used to return prosthesis 10 to an unflexed position when the moment is removed. Transverse rotation occurs when the wearer changes direction and, to a lesser degree, during the cycle of each step, as the wearer's pelvis twists slightly from side to side. The ability of the present prosthesis to accommodate such transverse rotation and to yield more easily to smaller degrees of rotation enhances the comfort and stability of the prosthesis.

It will be understood that the prosthesis of the present invention is capable of rotation about two or more axes simultaneously. Within the mechanical limitations of swivel joint 61, rotation of the joint about any one axis has no effect on its rotation about the other two axes. An advantage of the joint of the present invention lies in the fact that it closely simulates the range of motion of an anatomical foot. Shaft 54 within inner race 63 allows a greater degree of flexure about the x axis than is allowed about either the y or z axes. This dissimilarity corresponds to the range of motion allowed by an anatomical ankle.

According to a second embodiment shown in FIG. 13, connector 40, T-nut 42, and bolt 44 may be eliminated and replaced with an integral prosthetic shin. In this embodiment, the lower leg and shell 90 are formed from a single molded piece of fiber glass. The elimination of the metal connection therebetween results in a desirable weight savings. The adjustability of the connection that is achieved by the connector 40 with its four curved attachment faces 51 is lost, but the integration of the lower leg with shell 90 can be customized to duplicate the optimal relation of the lower leg to shell 90 for each wearer.

Referring still to FIG. 13, this alternate prosthetic foot comprises a foot 120, an ankle joint 130, a lower leg 140, and a connector 150. Foot 120 and ankle 130 are virtually the same as foot 20 and ankle 30 described above and shown in FIGS. 1–12. A shell 190 encloses ankle joint 130 in the manner of shell 90 discussed above. Connector 150 may be either male or female, as is discussed in greater detail below.

In place of a connector 40 affixed to shell 90 as above, however, lower leg 140 is molded as a single piece that is integral with shell 190. Like shell 190, lower leg 140 comprises fiberglass impregnated with epoxy.

Lower leg 140 comprises a hollow tube, thereby ensuring maximum strength with minimum mass. Lower leg 140 is preferably formed during the shell molding steps described above. To form lower leg 140, a preformed tube 141 (shown in FIGS. 14–15) is positioned with one end adjacent to the wax cast described above. The preformed tube is preferably wrapped with one layer of 6 oz. unidirectional glass fiber and placed in a mold. The fiberglass layers in shell 190 are modified to include layers that form and support the rigid joint between lower leg 140 and shell 190, as well as lower leg 140 itself. When the lower leg and shell have been impregnated with epoxy, they are removed from the mold. The preformed tube remains a part of, and forms the inside diameter of, lower leg 140.

In a preferred embodiment, the preformed tube is constructed of a bi-directional glass fiber impregnated with epoxy, such as G-10 glass cloth epoxy sheet. G-10 is manufactured by Westinghouse, Norplex, Spalding, and other manufacturers of epoxy fiberglass, and is widely available. G-10 has the necessary strength and durability for the present application. Other lightweight materials having similar physical properties may be substituted for the G-10 without departing from the spirit of the invention.

Referring now to FIG. 14, the upper end 142 of lower leg 140 is affixed to a male connector 160. In the preferred embodiment, the inside diameter 143 of the upper end of lower leg 140 is tapered, gradually increasing until it approximately equals the outside diameter of inner tube 141. Preferably, the degree of taper is small, for example traversing the axis of leg 140 at an angle of approximately 4 degrees. This tapered portion forms a conical annular shoulder 144 and a flat annular shoulder 145.

Still according to a preferred embodiment, connector 160 comprises a male lower portion 162, a coaxial adjacent female upper portion 164, and a central bore 166. Upper portion 164 comprises a rounded, annular shoulder 168, having a plurality of evenly circumferentially spaced radial bores 170 therethrough. Bores 170 are internally threaded and sized to receive an equal number of set screws 172. Preferably, there are four bores 170, spaced 90 degrees apart around shoulder 168.

Lower portion 162 of connector 160 comprises a tube 174 having a tapered outside diameter 175. The degree of taper equals the degree of taper of the inside diameter of lower leg 140. The tapered portion of connector 160 forms a conical annular shoulder 176, which corresponds to annular shoulder 144 of lower leg 140. Annular shoulder 168 of connector 160 forms a flat annular surface 177, which corresponds to flat annular shoulder 145 of lower leg 140. Hence, when lower portion 162 of connector 160 is inserted into the upper end of lower leg 140, shoulder 176 seats on shoulder 144, and flat annular surface 177 seats on flat annular shoulder 145, thereby centering and mounting connector 160 within lower leg 140. In practice, cement is applied to the shoulder surfaces, so that connector 160 and lower leg 140 are permanently joined.

Figure 2:
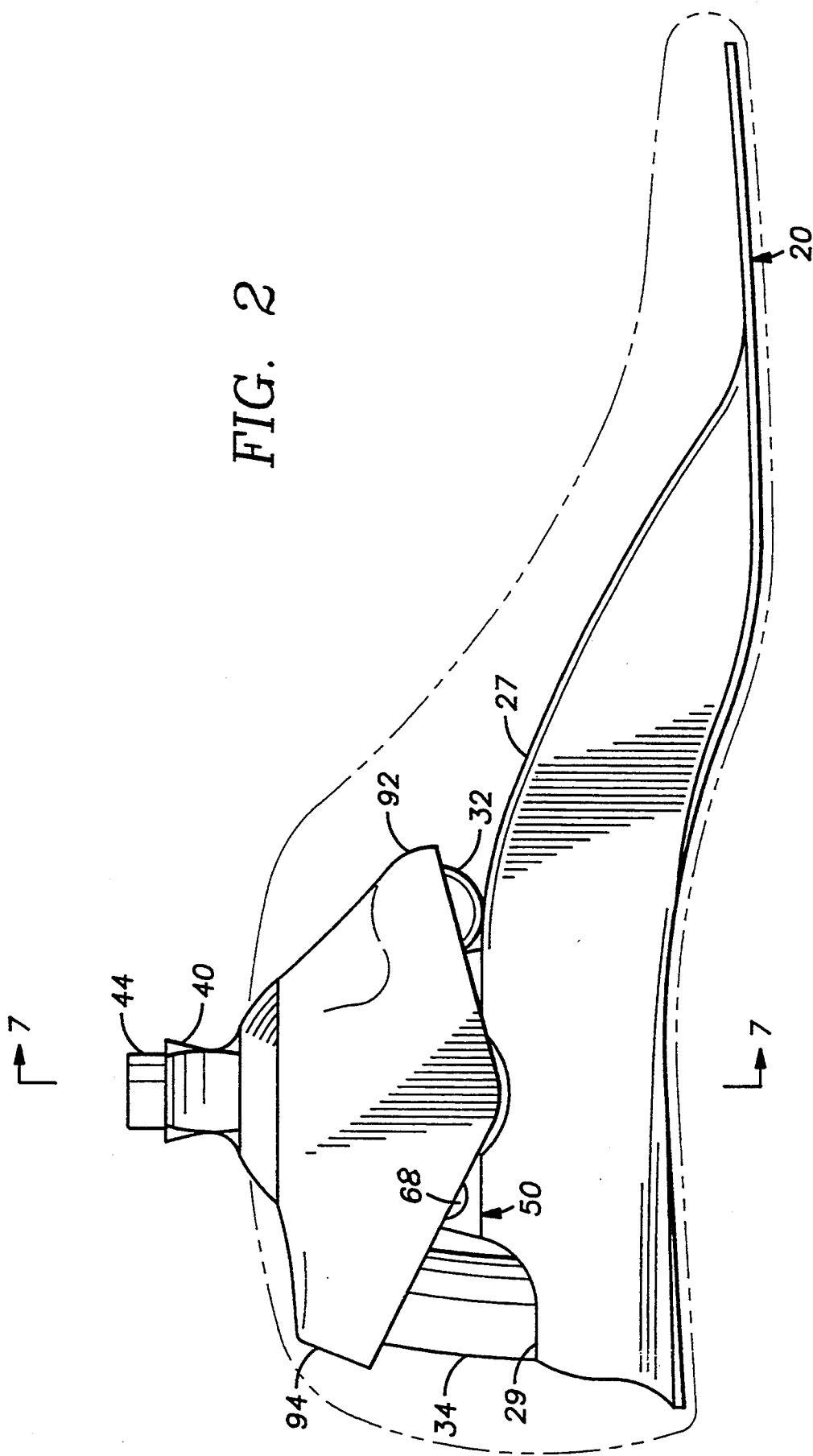
FIG. 2 is a side elevational view of the prosthetic foot of FIG. 1.

The configuration of connector 160, i.e., having four opposed set screws 172, allows it to receive and be rigidly affixed to a standard four-sided male connector, such as connector 40 shown in FIGS. 1 and 2. Such a connector would typically be used to attach a knee joint to the prosthetic lower leg.

As shown in FIG. 15, a female connector 180 may be used in place of connector 160. Connector 180 comprises a female lower portion 182 that receives upper end 142 of leg 140, a coaxial female upper portion 184, and a central bore 186 therethrough. Upper end 184 includes a plurality of circumferentially spaced built-up shoulders 188, each having an internally threaded bore 191 therethrough. Bores 191 are sized to receive set screws 192.

The circumference of lower portion 182 includes a partial longitudinal gap 194. On either side of gap 194 is a bracket 196, extending perpendicular to the outside wall of lower portion 182. Brackets 196 include opposing bores 198 (not shown) therethrough, so that when a tightening means, such as a bolt 200, is inserted through bores 198 and tightened, gap 194 closes and lower portion 182 tightens around the upper end of leg 140.

In operation, connector 180 is placed over the upper end 142 of lower leg 140, with lower leg 140 extending into central bore 186. Bolt 200 is tightened, causing the lower portion 182 of connector 180 to tighten around lower leg 140. In this manner connector 180 is affixed to lower leg 140. The upper portion 184 of connector 180 is adapted to receive a standard four-sided male connector, and operates in substantially the same manner with respect to the knee joint as does the upper portion 164 of connector 160, described above.

The difference between annular shoulder 168 of connector 160 and the four built-up portions 188 of connector 180 is a matter of weight and ease of machining. One skilled in the art will understand that there are several ways of housing and supporting the set screws and that the shin/knee connectors may be modified from the configurations described above without departing from the spirit of the invention.

While a preferred embodiment of the invention has been shown and described, modifications thereof can be made by one skilled in the art without departing from the spirit of the invention. For example, the precise shape of the components, the materials of which they are constructed, the degree of motion that is allowed in each direction, and other aspects of the invention can be changed without departing from the spirit of the invention.

What is claimed is:

1. A lightweight foot prosthesis, comprising:
   an integral foot having a heel, a toe, and a raised instep, said instep including a dorsal surface and a plantar surface;
   an ankle joint affixed to said foot and capable of motion around each of three perpendicular axes;
   means for limiting rotation of said ankle joint; and
   means for connecting said ankle joint to a leg;
   said ankle joint comprising a body, a swivel means housed in said body, a shaft rotatably mounted in said swivel means, and means for transmitting a force from the leg to said shaft, said rotation limiting means being disposed between said shaft and said body;
   said swivel means including a housing having a transverse main bore therethrough, an outer race fixed herein, and an inner race rotatably housed in said outer race, said inner race having a central bore therethrough, said bore being sized to receive said shaft;
   said rotation limiting means comprising a pair of annular compression mounts; and
   said housing including a pair of annular beveled seating faces, each such face centered on said main bore, each of said compression mounts being seated on one such face.

2. The foot prosthesis according to claim 1 wherein said foot comprises a molded copolymer.

3. The foot prosthesis according to claim 2 wherein said copolymer comprises approximately 90 percent polypropylene and approximately 10 percent polyethylene.

4. The foot prosthesis according to claim 1 wherein said instep includes a longitudinal groove adjacent said plantar surface.

5. The foot prosthesis according to claim 1 wherein said toe is substantially flat.

6. The foot prosthesis according to claim 1 wherein said compression mounts comprise a tough, resilient material.

7. The foot prosthesis according to claim 1 wherein said force transmitting means comprises a joint shell affixed to said shaft such that tilting of the shell causes said shaft to swivel within said swivel means.

8. The foot prosthesis according to claim 7 wherein said dorsal instep surface includes a forward planar surface and a rear planar surface, further including second and third rotation limiting means positioned between said forward and rear planar surfaces and said shell, respectively.

9. The foot prosthesis according to claim 8 wherein said second rotation limiting means includes a transversely mounted forward snubber.

10. The foot prosthesis according to claim 9 wherein said third rotation limiting means includes a vertically mounted rear snubber.

11. The foot prosthesis according to claim 1 wherein said connection means comprises a lower leg prosthesis integral with said force transmitting means.

* * * * *